United States Patent
Douglas-Hamilton et al.

(10) Patent No.: US 7,807,452 B2
(45) Date of Patent: Oct. 5, 2010

(54) DEVICE AND METHOD OF MAINTAINING SPERM MOTILITY IN A CAPILLARY-LOADED CHAMBER

(75) Inventors: Diarmaid H. Douglas-Hamilton, Beverly, MA (US); Meg D. Hamilton, Beverly, MA (US)

(73) Assignee: Hamilton Thorne, Inc., Beverly, MA (US)

( * ) Notice: Subject to any disclaimer, the term of this patent is extended or adjusted under 35 U.S.C. 154(b) by 121 days.

(21) Appl. No.: 12/330,228

(22) Filed: Dec. 8, 2008

(65) Prior Publication Data

US 2009/0142795 A1 Jun. 4, 2009

Related U.S. Application Data

(63) Continuation of application No. 11/525,366, filed on Sep. 22, 2006, now abandoned.

(60) Provisional application No. 60/719,392, filed on Sep. 22, 2005.

(51) Int. Cl.
*C12M 1/34* (2006.01)
*C12M 3/00* (2006.01)

(52) U.S. Cl. .................................. 435/288.3

(58) Field of Classification Search .................. 435/29, 435/288.3; 436/63; 422/102
See application file for complete search history.

(56) References Cited

U.S. PATENT DOCUMENTS 4,790,640 A * 12/1988 Nason ........................ 359/396
4,896,967 A * 1/1990 Douglas-Hamilton et al. .... 382/128

OTHER PUBLICATIONS

Loffier, Helmut; Johann Rastetter; Atlas of clinical Hematology, 1999, chapter 1, p. 4.*

* cited by examiner

*Primary Examiner*—Walter D Griffin
*Assistant Examiner*—Shanta G Doe
(74) *Attorney, Agent, or Firm*—Stroock & Stroock & Lavan LLP

(57) ABSTRACT

The invention relates, generally, to a method of removing sharp edges from a microscope coverslip comprising grinding down the edges and polishing the edges The invention also relates to a device for determining cell motility comprising a slide, a coverslip, comprising at least one edge that has been smoothed and a chamber, created by the slide and the coverslip and which is tangential to the coverslip, such that motile cells entering the chamber are substantially undamaged. The invention also relates to a method for using the device to determine cell motility.

11 Claims, 3 Drawing Sheets

CAPILLARY-LOAD CHAMBER

# US 7,807,452 B2

DEVICE AND METHOD OF MAINTAINING SPERM MOTILITY IN A CAPILLARY-LOADED CHAMBER

The present application is a continuation of U.S. patent application Ser. No. 11/525,366, filed Sep. 22, 2006 now abandoned which claims priority to Provisional Application Ser. No. 60/719,392 filed on Sep. 22, 2005.

INTRODUCTION

The invention relates, generally, to a method of removing sharp edges from a microscope coverslip comprising grinding down the edges and polishing the edges. The invention also relates to a device for determining cell motility comprising a slide, a coverslip, comprising at least one edge that has been smoothed and a chamber, created by the slide and the coverslip and which is tangential to the coverslip, such that motile cells entering the chamber are substantially undamaged. The invention also relates to a method for using the device to determine cell motility.

BACKGROUND OF INVENTION

Measurement of sperm motility (fraction of motile cells) is of considerable importance in the animal breeding market. The reason is that motility is a measure of the animals breeding effectiveness, since only motile sperm can fertilize the ovum. For a given number of sperm required per insemination dose, a higher motility means that the sample can be diluted more and therefore spread around to more females for breeding. This reduces the breeding cost and increases breeding efficiency. Therefore accurate determination of sperm motility is economically important.

Capillary-loaded chambers are frequently used for sperm sample examination. A chamber is created by placing a coverslip onto a microscope slide. The area between the slide and the coverslip is the chamber. Typically (e.g. in the Leja-4 chamber), a glass coverslip is fixed in position by ink strips, at a separation of 20 μm above a glass microscope slide. The 20-μm space thus formed between the two sheets of glass is divided into chambers (usually 2 or 4), each of which may be independently used for sperm sample analysis. The sperm sample is introduced at the entrance, and capillary action in the 20 μm gap sucks the sample into the chamber. It is then examined by microscope, and may be used for computer-assisted sperm analysis (CASA), for example with the IVOS analyzer. The IVOS measures the position of each sperm in a field of view. It then repeats the measurement at intervals of $\frac{1}{60}$ seconds, thus determining static and motile sperm count and velocity. The advantage of the capillary-load chamber is that it measures concentration of motile sperm cells accurately, allows rapid loading and analysis and is disposable.

A radially-loaded chamber (e.g., the Makler chamber) uses four posts to maintain a coverslip 10 μm above the slide surface, and is loaded by placing a drop on the sample platform. The cover is then placed on top of the platform. In contrast to the capillary-loaded chamber, the sample then spreads radially and is not loaded by capillary action. The sample is then examined visually or by CASA. A defect of the radially-loaded chamber is that the coverslip is not constrained and can therefore rise up, increasing the chamber depth. A particle only one micron in diameter on the posts will cause an error of 10% in the concentration calculation from the radially-loaded chamber. Moreover, after use, the chamber has to be cleaned, and its operation is consequently slower and the resulting concentration calculation is less accurate than the disposable capillary-loaded chambers.

Recently it has been found that sperm samples loaded into a radially-loaded chamber show higher motility than in the capillary-loaded chamber. The sperm sample consistently shows approximately 15% higher initial motile fraction in the radially-loaded than in the capillary-loaded chamber. Sperm velocity and other sperm motion parameters are not significantly altered. Since successful animal breeding depends on accurate motility measurement, it is important to determine if the decrease in motility in the capillary-loaded chamber is an artifact, and, if so, whether it can be eliminated. Possible causes include the greater chamber depth, potential toxic effects in the fixed-coverslip chambers, and possible damage to sperm during the capillary inflow loading phase.

Accordingly, it is desirable to provide an improved disposable capillary-loaded chamber design which provides an accurate and reliable sperm motility count and allows for rapid loading and analysis. The embodiments of the present invention represent an improvement to the capillary-loaded chamber design which prevents the reduction in motility observed in comparison to the radially-loaded chamber. It therefore increases the accuracy of sperm analysis using capillary-loaded chambers and allows more accurate and efficient animal breeding to be practiced.

SUMMARY OF THE INVENTION

Embodiments of the present invention satisfy the foregoing, as well as other, needs. In accordance with one embodiment of the present invention, there is provided a method of removing sharp edges from a microscope coverslip comprising grinding down the edges and polishing the edges.

In accordance with another embodiment of the present invention, there is provided a device for determining cell motility comprising a slide, a coverslip, comprising at least one edge that has been smoothed and a chamber, created by the slide and the coverslip and which is tangential to the coverslip, such that motile cells entering the chamber are substantially undamaged. In yet another embodiment of the present invention there is provide a method for using the device to determine cell motility.

BRIEF DESCRIPTION OF THE DRAWINGS

The invention will now be described with reference to the accompanying drawings, in which.

DETAILED DESCRIPTION OF THE PREFERRED EMBODIMENTS

Figure 1:
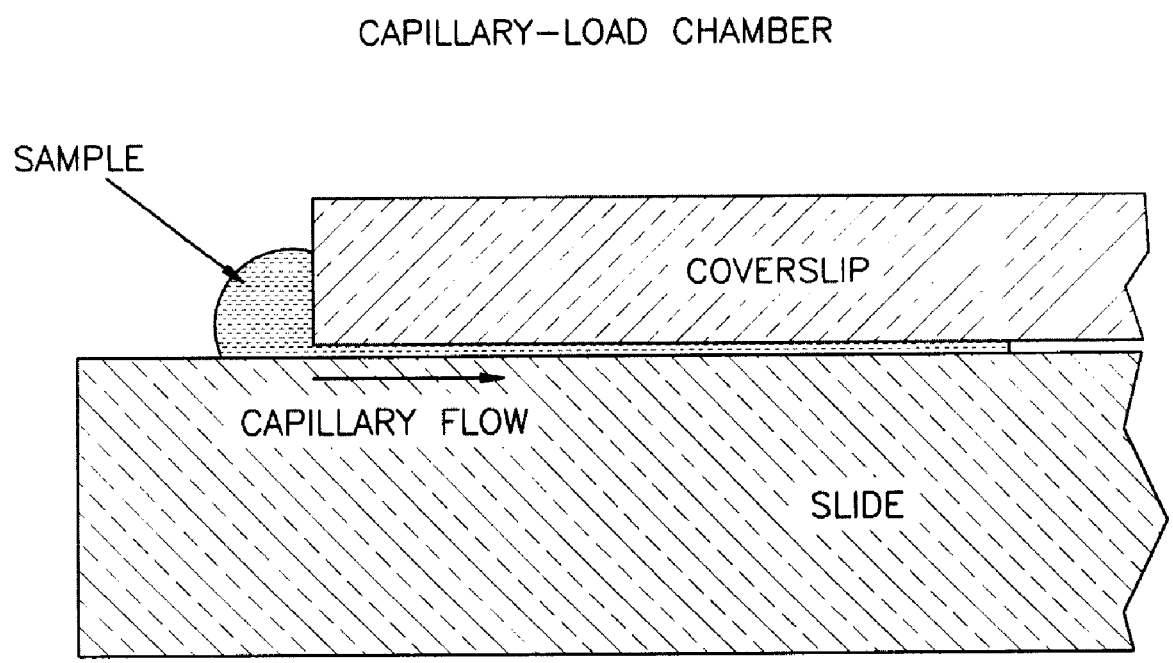
FIG. 1 shows a capillary load chamber, approximately to scale. The sample is placed at entrance and moves in by capillary action.

A capillary-loaded chamber such as the Leja-4 20 μm slide is shown in FIG. 1. The coverslip is held to the slide with adhesive ink spacers (not shown), which maintain the required 20 μm chamber depth. The sample is introduced by placing a drop at the edge of the coverslip. The sample is then drawn into the chamber by capillary action, typically filling it in 2-3 seconds. The flow velocity at the entrance constriction is approximately 25 mm/sec, more than 200 times faster than the normal sperm swimming speed. After filling is complete, any excess sample is wiped off to avoid drift.

Slides of this type have been used for 20 years for examining human sperm samples and have recently been adapted to animal breeding specimens. Human sperm are less dense and swim more slowly than bovine, porcine and equine sperm, and they are normally in a considerably more viscous medium than that use for examining animal sperm. No differences have been reported between human samples in Makler chambers and capillary slides. It is only with animal samples that the motility difference between Makler chamber and capillary slide has become apparent.

Surprisingly, it was determined that the motility difference between capillary-loaded and radially-loaded chambers is not due to toxicity. If sperm toxicity was a factor then sperm velocity and motion would be affected. Experiments showed that velocity and other motion parameters were not changed, indicating that toxicity was not a factor. In addition, the decrease in motility with time is slow following chamber loading indicating that something besides sperm toxicity was involved.

The lower sperm motility observed in the capillary-loaded chamber is also unlikely due to damage caused by sperm tumbling in the high transverse velocity gradient of the Poiseuille inflow stream, since reducing entry velocity (which reduces the velocity gradient) does not increase motility. The decreased motility appears to be due to the large animal sperm being scraped or cut on the sharp edge of the coverslip at the chamber entrance, as they are caught in the streamlines and moved into the chamber. Typical bovine sperm are approximately 100 µm in length, and sperm swimming freely in the sample have to enter the narrow 20 µm chamber gap at high velocity. It appears likely that a certain fraction of the sperm may be damaged by the sharp coverslip edge during entry. The damage would probably occur on the tail, and therefore would be likely to affect the motility.

Figure 2:
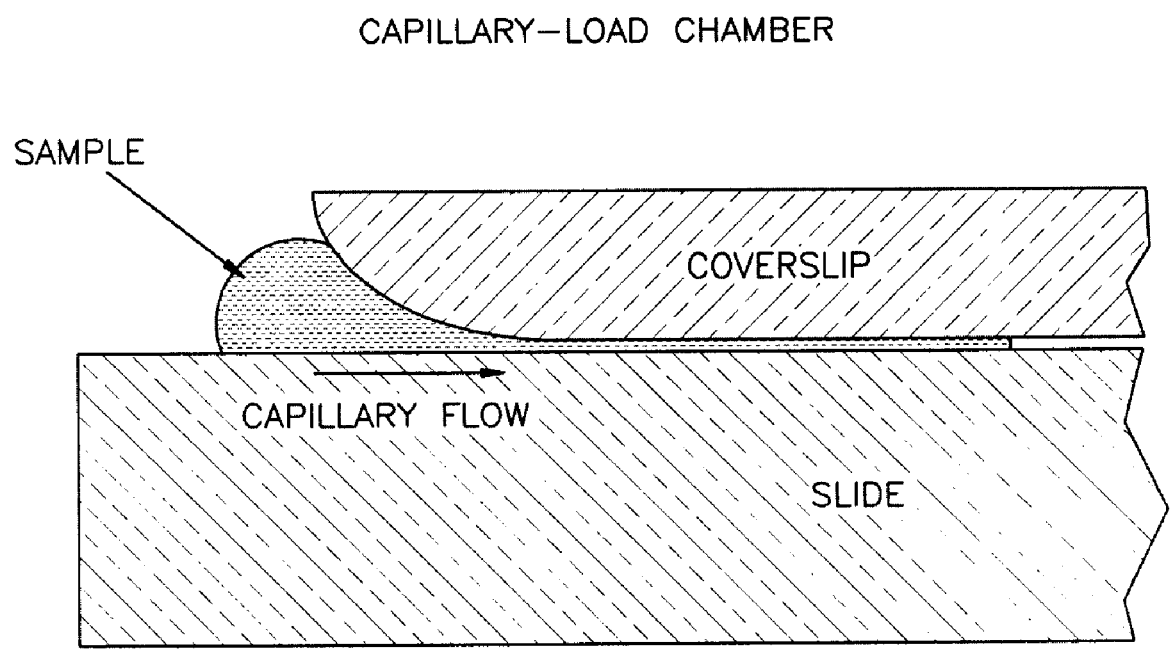
FIG. 2 shows a capillary load chamber with smoothed entry coverslip.

To test this possibility, we prepared coverslips in which the sharp edge was ground down, and used them in a capillary-load geometry, spaced 20 µm above the slide. The modification is shown in FIG. 2. The ground glass surface was polished, using techniques known in the art including but not limited to diamond grinding and emery paper filing and/or buffing, until any sharp edges or discontinuities were removed. The surface of the coverslip was further polished using techniques know in the art including but not limited to flaming, rouge buffing or laser polishing. The resulting smooth coverslip edge is tangential to the upper surface of the chamber, parallel to the slide, with a mean angle of about 24° to the sampling plane. The coverslip ground glass surface is a curve asymptoting smoothly toward the lower coverslip surface, and the sample therefore flows in without dragging sperm over sharp edges. Consequently damage to sperm from the sharp edge should be eliminated. Velocity of inflow remains unchanged.

The following examples are given for purposes of illustration only and are not intended to be construed in a limiting manner.

Example 1

Effect of Correction on Motility

Figure 3:
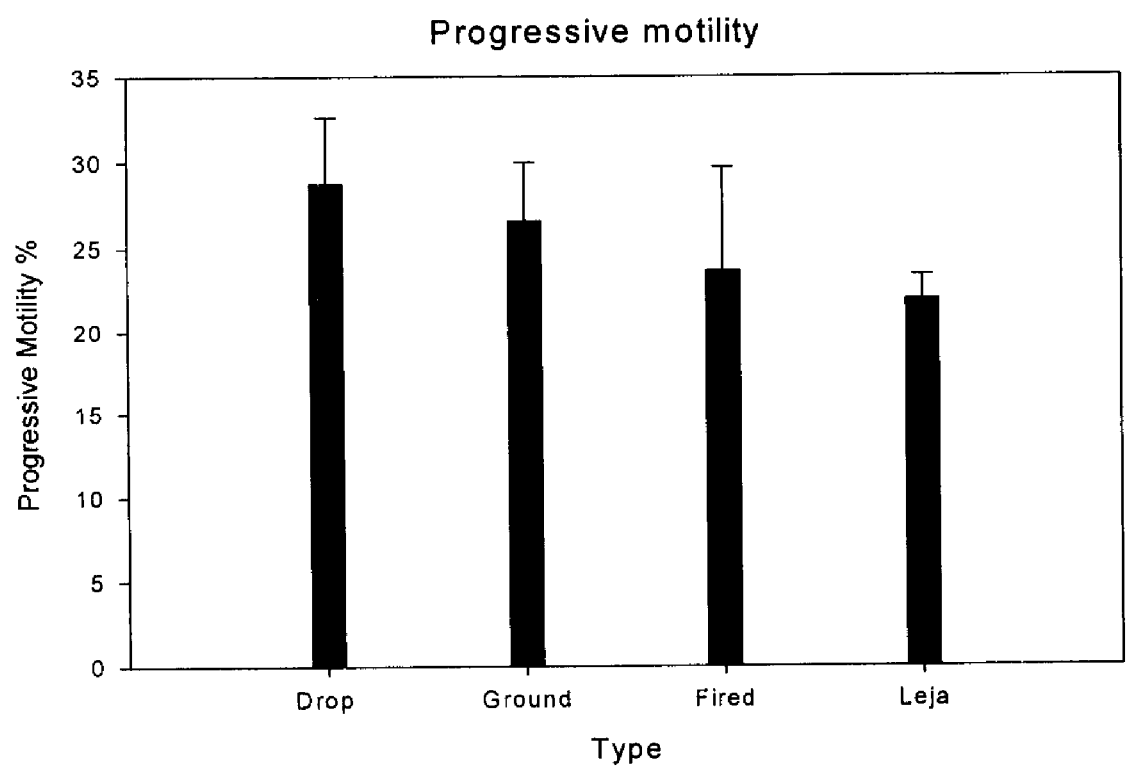
FIG. 3 is a graphic representation of progressive motility averaged over 4, 5, 3 and 2 runs for each type, respectively.

The motion parameters of a thawed bovine sperm sample were measured in an IVOS analyzer, with 1.75× multiplier, giving a net magnification of 17.5×. All slides had corrected smoothed coverslips and were maintained at 37° C. Fired coverslips, in which the sharp edges were removed by melting in a butane flame instead of by grinding, were also used for drop-loading and for capillary loading, as described below. Progressive motility, which is the fraction of cells with average path velocity (VAP)>75 µm/sec and path straightness (STR)>50%, and the standard deviations are shown in FIG. 3 for four types of loading methods described below.

Drop Load Method: 23 µl of sample were dropped on a microscope slide, not loaded by capillary action, and a fired coverslip was placed on it, with 20 µm spacers to maintain 20 µm chamber depth. The fired coverslip had been heated in a flame to melt the glass edge. The slides and coverslips were the same as those used in building Leja chambers.

Ground Method: The coverslip was ground to 24° angle of entry, positioned with spacers above slide, and 23 µl sample placed on the edge, then wiped off after capillary load.

Fired Method: The coverslip was fired in a butane flame to soften its edges. It was then positioned on the slide with spacers and loaded with 23 µl by capillary action, then wiped off.

Leja Method: Standard Leja slide is loaded with 3 µl, then wiped off.

All samples are placed in IVOS after 45 sec. However, the Ground and Fired capillary-loaded methods showed considerable drift which lasted for 1-2 min after loading. Initiation of analysis was delayed until sample drift ceased, because this could lead to motility decrease. Samples were rejected if drift lasted 3 minutes.

Details of the Drop Load, Fired, Ground and Leja method runs, with means and standard deviations, are shown in Table 1 and Table 2. Mean values averaged over the runs of each type are given.

TABLE 1

| Type | Mean No. Runs | Fill Time Sec.s | Temp ° C. | Fields | VAP | VCL | Mean # cells counted | CONC (millions/cm$^3$) |
|---|---|---|---|---|---|---|---|---|
| Drop Load | 4 | 5 | 37.1 | 10.0 | 81.7 | 157.9 | 494.3 | 37.0 |
| Fired | 3 | 3.3 | 37.3 | 10.0 | 78.6 | 152.9 | 496.3 | 37.2 |
| Ground | 5 | 4.6 | 37.1 | 9.8 | 81.5 | 155.1 | 507.2 | 38.7 |
| Leja | 2 | 2.5 | 37.2 | 10.0 | 79.0 | 163.4 | 438.0 | 32.8 |

Fields = number of regions photographed
VAP = average path velocity
VCL = average curvilinear velocity (µm/sec)

TABLE 2

| Type | MOT Count | MOT Conc (millions/cm$^3$) | Mean MOT | SD MOT | Mean Prog % | SD Prog |
|---|---|---|---|---|---|---|
| Drop Load | 328.5 | 24.6 | 66.3 | 4.2 | 28.8 | 3.9 |
| Fired | 270.0 | 20.2 | 54.0 | 6.1 | 23.7 | 6.0 |
| Ground | 310.6 | 23.7 | 61.0 | 2.5 | 26.6 | 3.4 |
| Leja | 248.0 | 18.6 | 56.5 | 2.1 | 22.0 | 1.4 |

MOT Count = number of motile cells counted
Mean MOT = mean motile % of total cells counted
SD MOT = standard deviation of mean MOT
Mean Prog % = Mean progressive motility %
SD Prog = standard deviation of progressive motility %

As indicated by the VCL, the sperm velocity is virtually unchanged, implying that the sperm are not crippled or damaged by the loading technique. However, the Ground method shows progressive motility which is 92% of that seen using the Drop Load method. The Leja values are only 76% of the Drop Load value. The low Leja Method value is probably attributed to the uncorrected sharp coverslip edge which damages sperm entering the chamber. The remaining 8% deficit is likely to be due to the drift delay time of 1-2 minutes before analysis on the ground type cases.

The Fired Method showed slight improvement over the Leja Method, but the higher standard deviation is probably due to the difficulty in accurate firing of the coverslip edge. The Ground method showed greater improvement, and the combination of Ground and Fired to produce a truly smooth coverslip will likely result in further improvements.

In conclusion, damage to sperm occurs during loading from the sharp coverslip edge, and removal/smoothing of the edge will increase the sperm motility by as much as 20-30%. Damage can be avoided by using a properly ground coverslip edge, preferably also fire-polished.

We claim:

1. A device for determining cell motility comprising:
    a slide;
    a coverslip comprising at least one edge that is formed by a first surface of the coverslip having a continuous radius intersecting a second surface of the coverslip; and
    a chamber created by the slide and the first surface of the coverslip and which is tangential to the coverslip, such that motile cells entering the chamber are substantially undamaged.

2. The device of claim 1, wherein the motile cell is a sperm cell.

3. The device of claim 1, wherein the coverslip comprises glass or plastic.

4. The device of claim 1, wherein the chamber is capillary-loaded with motile cells.

5. The device of claim 1, wherein the coverslip is planar, intersecting the plane of the slide at an angle conducive to smooth fluid flow.

6. The device of claim 1, wherein the coverslip comprises a curve optimized for optimum laminar fluid flow.

7. A method for using a device for determining cell motility the device comprising: a slide; a coverslip comprising at least one edge that is formed by a first surface of the coverslip having a continuous radius intersecting a second surface of the coverslip; and a chamber created by the slide and the first surface of the coverslip and which is tangential to the coverslip, such that motile cells entering the chamber are substantially undamaged, the method comprising:
    loading a sample of cells onto the device via capillary action;
    counting the total number of cells;
    counting the total number of moving cells
    determining the ratio of the number of moving cells to the total number of cells.

8. A device for determining cell motility comprising:
    a slide having an upper surface;
    a coverslip comprising a lower surface and at least one edge that has been smoothed by removing sharp discontinuities therein, wherein the edge is a curve asymptoting smoothly toward the lower coverslip surface and wherein the smooth edge of the coverslip is tangential to the chamber, thereby creating a mean angle of about 24° to the upper surface of the slide; and
    a chamber created by the upper surface of the slide and the lower surface of the coverslip, the smoothed edge of the coverslip defining an entrance to the chamber, such that motile cells entering the chamber are substantially undamaged.

9. The device of claim 8, wherein the motile cell is a sperm cell.

10. The device of claim 8, wherein the coverslip comprises glass or plastic.

11. The device of claim 8, wherein the chamber is capillary-loaded with motile cells.

* * * * *